United States Patent [19]
Bzoch

[11] Patent Number: 5,790,981
[45] Date of Patent: Aug. 11, 1998

[54] PATIENT HIP GUARD

[75] Inventor: Jan J. Bzoch, South Pasadena, Fla.

[73] Assignee: Orthosis Corrective Systems Corp., Pinellas Park, Fla.

[21] Appl. No.: 538,554

[22] Filed: Oct. 3, 1995

[51] Int. Cl.$^6$ ................................................. A41D 13/00
[52] U.S. Cl. .................................................... 2/22; 2/455
[58] Field of Search ............................. 2/22, 23, 24, 2, 2/908, 911, 455, 456

Primary Examiner—Michael A. Neas
Attorney, Agent, or Firm—James E. Larson; Larson & Larson, P.A.

[57] ABSTRACT

A patient hip guard is designed to be worn inside or outside of the clothing of the user. The guard includes a hip pad on each side, sized and configured to cover each hip, and consisting of an aesthetically pleasing pocket containing a pad having a configuration designed to approximate the femoral head of the hip bone. The pads are connected together by a belt adjustable in length to account for varying waist sizes. The inventive guard includes no buckles or other hard components that could cause discomfort to the user.

11 Claims, 3 Drawing Sheets

PATIENT HIP GUARD

BACKGROUND OF THE INVENTION

The present invention relates to a patient hip guard intended to protect the user against breaking of a hip should the user accidentally fall.

In recent years, in the United States, more than 250,000 hip fractures have occurred annually. Most of these hip fractures occur as a result of falls with over 80% of such hip fractures occurring in older people. It has been estimated that medical costs and lost income resulting from hip fractures approach 10 Billion Dollars a year. As such, a need has developed for a device that will protect a person, when falling, against the possibility of a hip fracture.

Applicant is aware of a product sold under the Trademark "HipGuard" designed to be worn outside the user's clothing and including two oppositely disposed hip pads connected with a belt. In the "HipGuard", metallic buckles are employed which would render the "HipGuard" uncomfortable when worn under the clothing. Furthermore, no effort is made in the "HipGuard" to provide specific engineering design in the pads themselves to best distribute forces placed thereon during a fall to facilitate prevention of hip fracture.

SUMMARY OF THE INVENTION

The present invention relates to a patient hip guard. The present invention includes the following interrelated objects, aspects and features:

(A) In a first aspect, the inventive patient hip guard is designed with a belt having adjustable length and having two hip pads, each one of which is designed to overlie one of the hips of the user.

(B) The belt interconnecting the hip pads is made of a soft material, easily flexible, and including the use of hook and pile fastening means to permit adjustment of length. In this regard, a plastic ring is provided on one of the hip pads through which one end of the belt is threaded. The ring is so located on the inventive device that one of the hip pads shields the ring from engagement with the user's body to protect against engagement with the hard ring.

(C) The other hip pad also carries a plastic ring in a manner shielding it from the user's body, which ring is employed to receive the other end of the flexible belt allowing the inventive patient hip guard to be fastened about the waist of the user with the belt being adjustable for patients of differing waist sizes.

(D) Each hip guard includes an outer hard plastic exterior pad and an interior pad made of a material such as soft polyethylene having an inside relieved area sized and configured to approximate the femoral head of the hip bone.

(E) In the preferred embodiment of the present invention, the exterior and interior pads are contained within an aesthetically pleasing cover attached to the belt and, preferably, provided in a color coordinated with the color of the belt so that the inventive patient hip guard may be worn outside or inside the user's clothing.

Accordingly, it is a first object of the present invention to provide a patient hip guard.

It is a further object of the present invention to provide such a device including two opposed hip guards mounted on a belt devoid of any hard objects that could otherwise render the inventive device uncomfortable.

It is a yet further object of the present invention to provide such a device wherein each pad includes a hard exterior pad and a softer interior pad having a relieved area therein sized and configured to conform to the patient's femoral head.

It is a still further object of the present invention to provide such a device including the use of hook and pile fastening means to allow adjustability of the length of the belt.

These and other objects, aspects and features of the present invention will be better understood from the following detailed description of the preferred embodiment when read in conjunction with the appended drawing figures.

SPECIFIC DESCRIPTION OF THE PREFERRED EMBODIMENT

Figure 1:
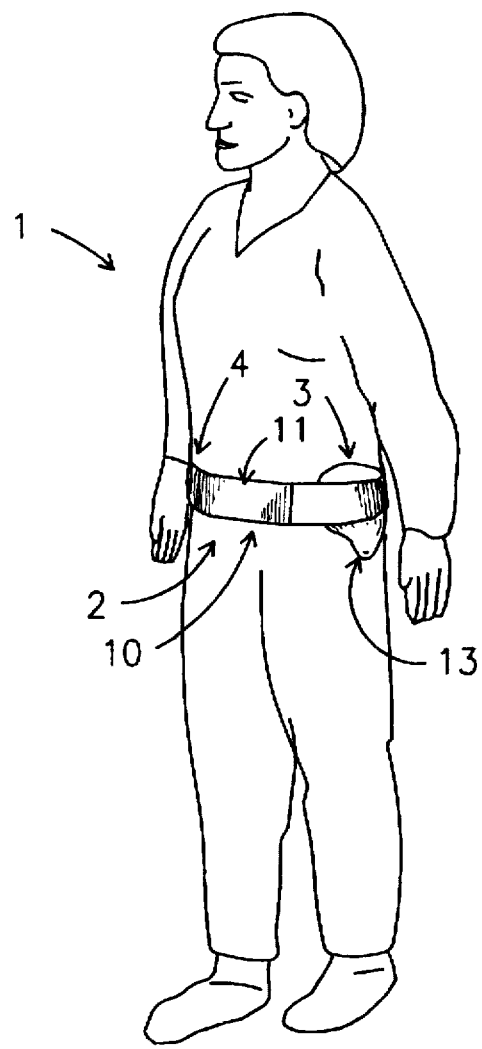
FIG. 1 shows a perspective view of the present invention shown attached about the waist of a user.

With reference, first, to FIG. 1, the user is generally designated by the reference numeral 1 and is seen to include a waist area 2 with hips 3 and 4. The present invention is generally designated by the reference numeral 10 and is seen to include a belt 11 and pads 13 and 15 of which only the pad 13 is visible in FIG. 1.

Figure 3:
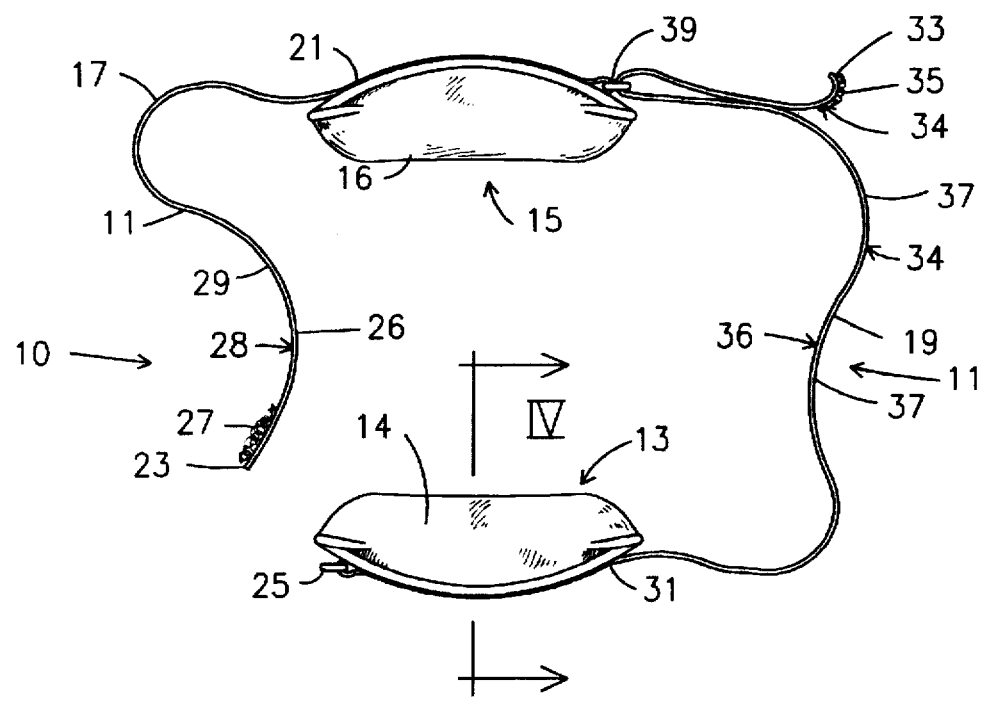
FIG. 3 shows a top view of the present invention.

With particular reference to FIG. 3, it is seen that the belt 11 consists of a first strap 17 and a second strap 19. The first strap 17 has a first end 21 fixedly secured to the outer covering 16 of the pad 15 and has a second free end 23. The outer covering 14 of the pad 13 carries a ring 25 sized and configured to receive the second end 23 of the strap 17 therethrough. At the second end 23 of the strap 17, hooks 27 of a hook and pile fastening means are suitably disposed on one face 28. The other face 26 is devoid of fastening means. On the same face 28 of the strap 17, adjacent to the hooks 27 and extending along the rest of the length of that face 28 of the strap 17, the pile portion 29 of hook and pile fastening means is suitably disposed. In this way, the second end 23 of the strap 17 may be extended through the ring 25 whereupon it may be folded upon itself with the hook portion 27 engaging the pile portion 29 in folded up configuration to fasten the strap to the pad 13.

With further reference, in particular, to FIG. 3, the strap 19 has a first end 31 fixedly secured to the outer covering 14 of the pad 13. The second end 33 of the strap 19, on face 34, is covered with the hook portion 35 of a hook and pile fastening means with the remainder of that face 34 of the strap 19 being covered with the pile portion 37 of hook and pile fastening means. The face 36 is devoid of fastening means. The outer covering 16 of the pad 15 has a ring 39 through which, as shown in FIG. 3, the second end 33 of the strap 19 may be threaded whereupon the hook portion 35 may be engaged with the pile portion 37 of the hook and pile fastening means to fasten the strap 19 about itself.

As should be understood from FIGS. 1 and 3, one of the straps 17 or 19 extends around the back portion of the waist of the user whereas the other of the straps 17 and 19 extends around the front of the waist of the user. For purposes of explanation, presuming that the strap 19 extends around the back of the waist of the user, the effective length of the strap 19 may be adjusted by releasing the hook portion 35 from the pile portion 37 and pulling the strap 19 through the ring 39 either in a direction lengthening the effective length of the strap 19 or shortening it, as the case may be, to adjust the length of the strap 19 across the back of the waist of the user so that the positions of the pads 13 and 15 are appropriately located overlying the respective femoral heads of the hips of the user. Thereafter, the second end 23 of the strap 17 may be pulled through the ring 25 to fasten the inventive device 10 snugly around the waist of the user with the pads 13 and 15 suitably overlying the hips thereof. Of course, these functions of the straps 17, 19 may be reversed. As should be understood from FIG. 3, the rings 25 and 39 are so located on the pads 13 and 15, respectively, that they are shielded from the body of the user preventing engagement of the hard rings 25 and 39 with the user's body so that the inventive device 10 may be comfortably worn under the clothing of the user, if desired, as well as over the clothing of the user.

Figure 2:
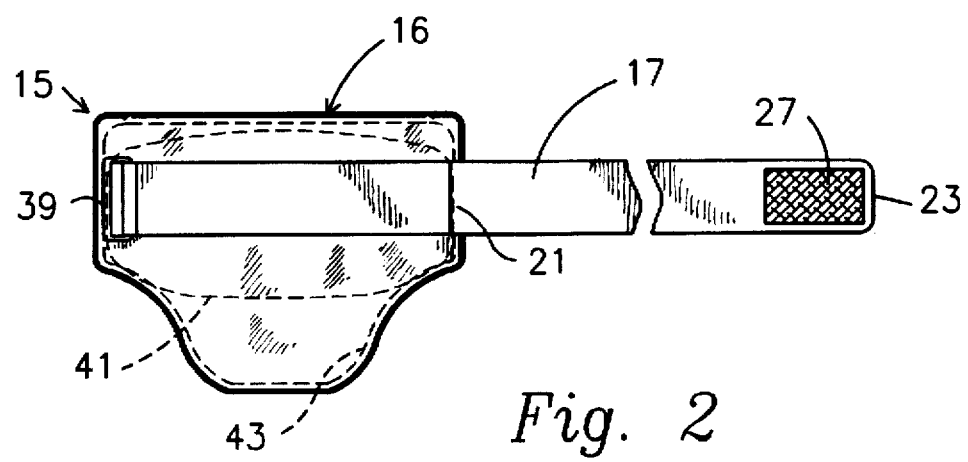
FIG. 2 shows a side view of the inventive device with the pads thereof shown in phantom.
Figure 6:
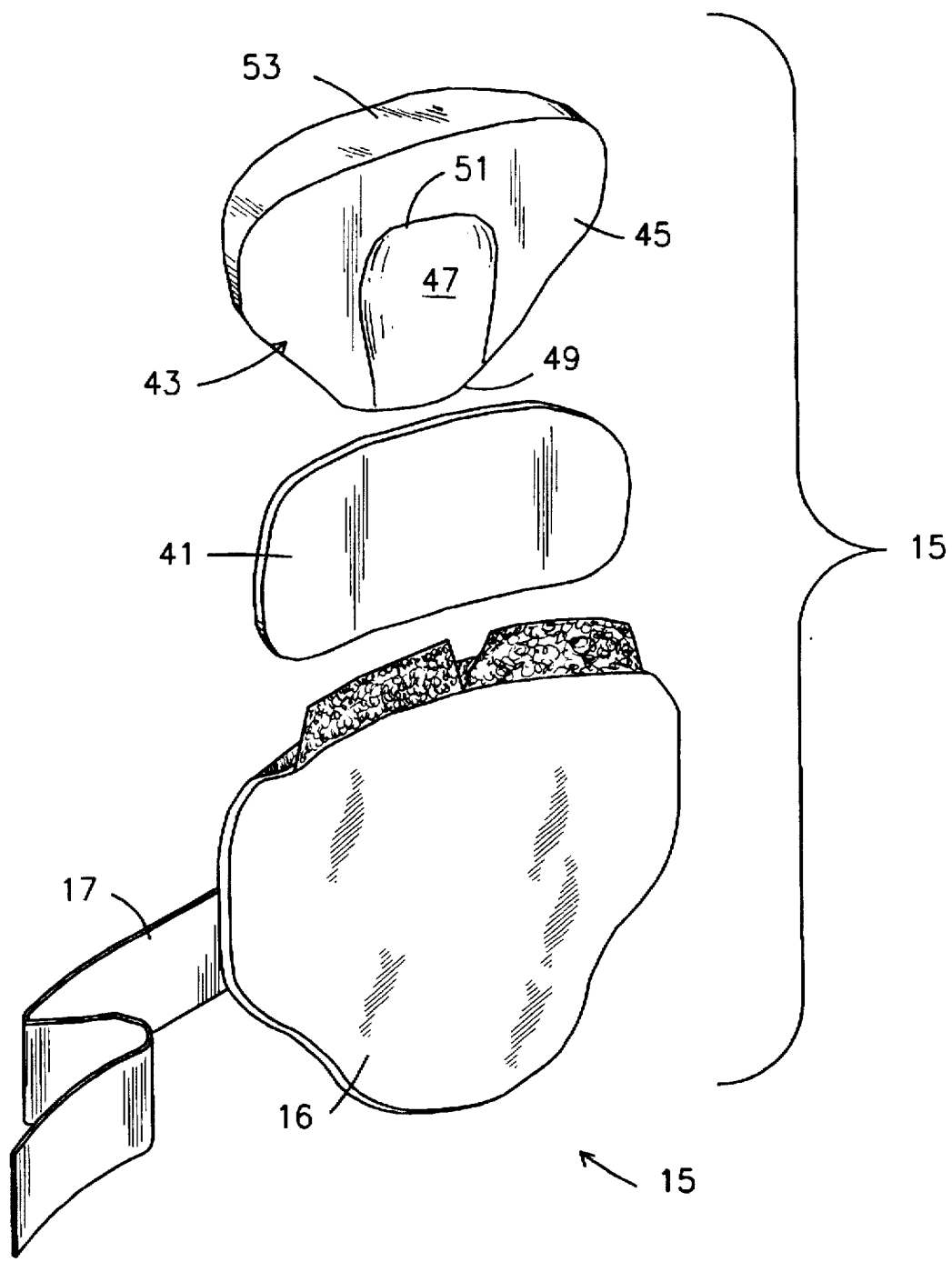
FIG. 6 shows a perspective view of a portion of the inventive device with the pad covering and pads shown in exploded view for detail.

With reference to FIG. 6, the pad 15 is shown in detail including the outer covering 16 defining an internal chamber 40, the outer hard pad 41 and the inner softer flexible pad 43 within the internal chamber 40. With reference to FIG. 2, the superpositioning of the outer pad 41 over the inner pad 43 is shown.

As seen in FIG. 6, the pad 43 has an inner surface 45 including a relieved region 47 extending from a bottom surface 49 upwardly into the surface 45 to a top termination 51 below the upper surface 53 of the pad 43. The relieved region 47 is sized and configured to correspond to the femoral head of the user's hip so that when the pad 15 is placed, by the straps 17 and 19, in overlying relation to the user's hip, the relieved region 47 overlies the femoral head of the user's hip to provide cushioning protection to the femoral head in such a manner that forces imposed on the pad 15, should the user fall on that side of their body, are spread around the user's hip in such a manner that the risk of fracture of the user's hip is significantly reduced.

Figures 4, 5:
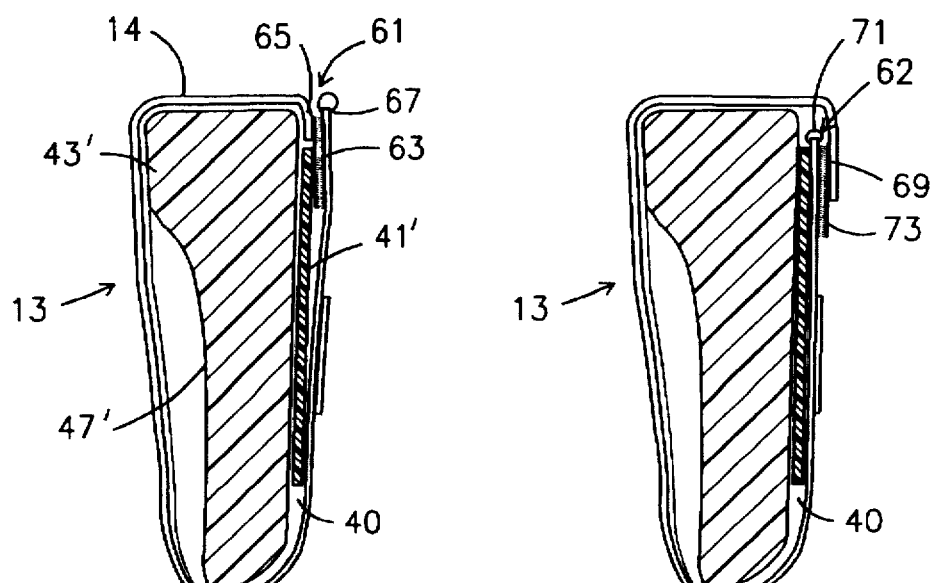
FIG. 4 shows a cross-sectional view along the line IV—IV of FIG. 3.
FIG. 5 shows a cross-sectional view similar to that of FIG. 4 but showing an alternative closure for the pad covering.

With reference to FIG. 4, the pad 13 is shown in cross-section and includes the outer covering 14, the outer relatively hard pad 41' and the inner relatively soft and resilient pad 43'. The relieved region 47' is shown in FIG. 4.

With further reference to FIG. 4, the outer covering 14 is seen to include an opening 61 which may be closed through the use of hook and pile fastening means 63, which opening allows access to the interior 40 of the outer covering 14 to permit insertion and removal of the pads 41' and 43'. In FIG. 4, the outer covering 14 has a portion 65 folded under another portion 67 with the hook and pile fastening means 63 being therebetween. In the embodiment illustrated in FIG. 5, the portion 69 overlies the portion 71 with hook and pile fastening means 73 being therebetween to fasten the opening 62 closed.

With the inventive patient hip guard having been described in great detail, its preferred manner of use should now be self-explanatory. The length of the strap 19 is adjusted in the manner explained hereinabove so that the pads 13 and 15 are placed over the hips of the user. The strap 17, second end 23 is extended through the ring 25 and then folded back upon itself to snugly fasten the inventive device 10 about the waist of the user with the pads 13 and 15 hanging down over the hips thereof to provide the desired protection.

As explained above, due to the shielding of the rings 25 and 39 from the user's body by the pads 13 and 15, respectively, no hard objects may come into contact with the user's body. Thus, the inventive device 10 may suitably be worn inside or outside the clothing of the user.

Furthermore, while the straps 17 and 19 have been described as having the hook portions 27, 35, respectively, of hook and pile fastening means on their respective ends 23 and 33, of course, if desired, the hook portions 27 and 35 may be replaced with pile portions with the remaining areas of the same surface of each strap 17 and 19 being covered with hook portions.

In the preferred embodiment of the present invention, the hard pads 41 and 41' are suitably made of a hard molded plastic material. Conversely, the softer interior pads 43 and 43' may be suitably made of a softer polyethylene which may or may not be foamed. Other foamable plastics may also suitably be used as well as other soft materials such as rubber of a low Shore A hardness. The straps 17 and 19 may be made of fabric, leather or plastic.

As such, an invention has been disclosed in terms of a preferred embodiment thereof which fulfills each and every one of the objects of the invention as set forth hereinabove and provides a new and useful patient hip guard of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

I claim:

1. A patient hip guard, comprising:
   a) a first hip pad and a second hip pad, each hip pad including a cover defining an internal chamber containing a resilient pad having a relieved region sized and configured in correspondence to a shape of a femoral head of a user's hip and adapted to overlie a femoral head of a user's hip when placed adjacent thereto;
   b) a first strap devoid of a hard object attached between said hip pads and being adjustable in length whereby a spacing between said hip pads may be adjusted;
   c) a second strap devoid of a hard object attached between said hip pads and being adjustable in length to accommodate to waists of differing sizes; and
   d) a rigid pad within the internal chamber engaging a face of a respective resilient pad opposite the relieved region.

2. The patient hip guard of claim 1, wherein said first strap comprises a first end fixedly attached to said first hip pad, a ring fixed on said second hip pad and a second end of said first strap extended through said ring and fastenable upon itself.

3. The patient hip guard of claim 2, said first strap having first and second faces, said first face having one half of a hook and pile fastening means disposed thereon adjacent said second end of said first strap, and, adjacent and proximal thereto, said first face having another half of said hook and pile fastening means disposed thereon whereby said first strap may be folded upon itself to interengage said hook and pile fastening means.

4. The patient hip guard of claim 2, wherein said ring is located on an outside surface of said second hip pad cover remote from a user when said patient hip guard is worn thereby.

5. The patient hip guard of claim 1, wherein said second strap comprises a first end fixedly attached to said second hip pad, a ring fixed on said first hip pad and a second end of said second strap extended through said ring and fastenable upon itself.

6. The patient hip guard of claim 5, said second strap having first and second faces, said first face having one half of a hook and pile fastening means disposed thereon adjacent said second end of said second strap, and, adjacent and proximal thereto, said first face having another half of said hook and pile fastening means disposed thereon whereby said second strap may be folded upon itself to interengage said hook and pile fastening means.

7. The patient hip guard of claim 5, wherein said ring is located on an outside surface of said first hip pad cover remote from a user when said patient hip guard is worn thereby.

8. The patient hip guard of claim 2, wherein said second strap comprises a first end fixedly attached to said second hip pad, a further ring fixed on said first hip pad and a second end of said second strap extended through said further ring and fastenable upon itself.

9. The patient hip guard of claim 1, wherein said resilient pad is made of foamed polyethylene.

10. The patient hip guard of claim 2, wherein said rigid pad is made of hard plastic.

11. A patient hip guard, comprising:

a) a first hip pad and a second hip pad, each hip pad including a cover defining an internal chamber containing a resilient pad having a relieved region sized and configured in correspondence to a shape of a femoral head of a user's hip and adapted to overlie a femoral head of a user's hip when placed adjacent thereto and a rigid pad engaging a face of a respective resilient pad opposite said relieved region;

b) a first strap attached between said hip pads and being adjustable in length whereby a spacing between said hip pads may be adjusted, said first strap comprising a first end fixedly attached to said first hip pad, a first ring fixed on said second hip pad and a second end of said first strap extended through said ring and fastenable upon itself;

c) a second strap attached between said hip pads and being adjustable in length to accommodate to waists of differing sizes, said second strap comprising a first end fixedly attached to said second hip pad, a second ring fixed on said first hip pad and a second end of said second strap extended through said ring and fastenable upon itself; and d) the cover having an opening closeable with hook and pile fastening means, the opening allowing access to the internal chamber to permit insertion and removal of the resilient pad and rigid pad.

* * * * *